(12) United States Patent
Egnelöv

(10) Patent No.: US 9,080,263 B2
(45) Date of Patent: Jul. 14, 2015

(54) MULTIFILAMENTS WITH TIME-DEPENDENT CHARACTERISTICS, AND MEDICAL PRODUCTS MADE FROM SUCH MULTIFILAMENTS

(75) Inventor: Per Egnelöv, Phuket (TH)

(73) Assignee: NOVUS SCIENTIFIC AB, Uppsala (SE)

( * ) Notice: Subject to any disclaimer, the term of this patent is extended or adjusted under 35 U.S.C. 154(b) by 346 days.

(21) Appl. No.: 13/370,433

(22) Filed: Feb. 10, 2012

(65) Prior Publication Data

US 2013/0211430 A1    Aug. 15, 2013

(51) Int. Cl.
| | |
|---|---|
| A61L 17/00 | (2006.01) |
| A61B 17/04 | (2006.01) |
| D02G 3/44 | (2006.01) |
| A61L 17/06 | (2006.01) |
| A61F 2/00 | (2006.01) |
| A61B 17/06 | (2006.01) |
| A61B 17/00 | (2006.01) |

(52) U.S. Cl.
CPC .......... *D02G 3/448* (2013.01); *A61B 17/06166* (2013.01); *A61F 2/0063* (2013.01); *A61L 17/06* (2013.01); *A61B 2017/00004* (2013.01); *A61B 2017/0618* (2013.01); *Y10T 428/2929* (2015.01); *Y10T 428/2931* (2015.01)

(58) Field of Classification Search
CPC ............. A61B 17/06166; A61L 17/00–17/145
USPC .......... 606/151, 224–231; 428/364, 373, 374, 428/397; 442/199–202, 305, 308–311, 361, 442/362, 366; 623/23.72, 23.75
See application file for complete search history.

(56) References Cited

U.S. PATENT DOCUMENTS

| | | | | | |
|---|---|---|---|---|---|
| 3,187,752 | A | * | 6/1965 | Glick | 606/231 |
| 3,463,158 | A | * | 8/1969 | Schmitt et al. | 606/154 |
| 3,636,956 | A | * | 1/1972 | Schneider | 606/224 |
| 3,797,499 | A | * | 3/1974 | Schneider | 606/230 |
| 3,949,755 | A | * | 4/1976 | Vauquois | 606/229 |
| 4,047,533 | A | * | 9/1977 | Perciaccante et al. | 606/230 |

(Continued)

FOREIGN PATENT DOCUMENTS

| | | |
|---|---|---|
| EP | 0905292 A1 | 3/1999 |
| EP | 2016956 A2 | 1/2009 |

(Continued)

OTHER PUBLICATIONS

European Search Report dated Sep. 6, 2012, (7 pgs.).

*Primary Examiner* — Ryan Severson

(74) *Attorney, Agent, or Firm* — Foley & Lardner LLP

(57) ABSTRACT

The invention relates to a resorbable multifilament comprising a number of individual resorbable filaments of a first type having a first degradation time and a number of individual resorbable filaments of a second type having a second degradation time, wherein the filaments of the first type and the filaments of the second type are arranged in close relationship to form a composite multifilament having a length and a specific composite cross-section comprising cross-sections of the individual filaments of the first type and second type, wherein the cross-sections of the individual filaments of the first and second type are located at determined relative positions, wherein the relative positions amongst the individual cross-sections of the filaments of the first and second types are invariant over the length of the composite multifilament.

19 Claims, 1 Drawing Sheet

(56) References Cited

U.S. PATENT DOCUMENTS

| | | | | |
|---|---|---|---|---|
| 4,127,696 A | * | 11/1978 | Okamoto | 428/373 |
| 4,430,383 A | * | 2/1984 | Smith et al. | 428/364 |
| 5,019,093 A | * | 5/1991 | Kaplan et al. | 606/228 |
| 5,405,682 A | * | 4/1995 | Shawyer et al. | 428/221 |
| 5,482,772 A | * | 1/1996 | Strack et al. | 428/357 |
| 5,688,582 A | * | 11/1997 | Nagaoka et al. | 428/198 |
| 5,718,972 A | * | 2/1998 | Murase et al. | 428/360 |
| 5,783,503 A | * | 7/1998 | Gillespie et al. | 442/340 |
| 6,045,571 A | * | 4/2000 | Hill et al. | 606/228 |
| 6,162,962 A | | 12/2000 | Hinsch et al. | |
| 6,284,680 B1 | * | 9/2001 | Aikawa et al. | 442/363 |
| 6,395,392 B1 | * | 5/2002 | Gownder | 428/370 |
| 6,624,100 B1 | * | 9/2003 | Pike | 442/340 |
| 6,716,234 B2 | * | 4/2004 | Grafton et al. | 606/228 |
| 6,743,506 B2 | * | 6/2004 | Bond et al. | 428/370 |
| 6,994,719 B2 | * | 2/2006 | Grafton | 606/228 |
| 7,029,490 B2 | * | 4/2006 | Grafton et al. | 606/228 |
| 7,294,406 B2 | * | 11/2007 | Canham et al. | 428/446 |
| 7,329,271 B2 | * | 2/2008 | Koyfman et al. | 606/228 |
| 7,357,810 B2 | * | 4/2008 | Koyfman et al. | 606/228 |
| 7,737,060 B2 | * | 6/2010 | Strickler et al. | 442/361 |
| 7,871,946 B2 | * | 1/2011 | Tsujimoto et al. | 442/361 |
| 8,012,171 B2 | * | 9/2011 | Schmieding | 606/228 |
| 8,012,172 B2 | * | 9/2011 | Grafton et al. | 606/228 |
| 8,016,841 B2 | | 9/2011 | Magnusson et al. | |
| 8,083,755 B2 | | 12/2011 | Mathisen et al. | |
| 8,088,146 B2 | * | 1/2012 | Wert et al. | 606/228 |
| 8,109,967 B2 | * | 2/2012 | Koyfman et al. | 606/232 |
| 8,257,393 B2 | * | 9/2012 | Cichocki, Jr. | 606/228 |
| 8,383,188 B2 | * | 2/2013 | Mazzocca et al. | 427/2.31 |
| 8,568,449 B2 | * | 10/2013 | Koyfman et al. | 606/232 |
| 8,636,767 B2 | * | 1/2014 | McClain | 606/230 |
| 8,672,966 B2 | * | 3/2014 | Wert et al. | 606/228 |
| 2001/0019931 A1 | | 9/2001 | Fare | 442/361 |
| 2001/0051814 A1 | | 12/2001 | Shalaby | 606/230 |
| 2002/0006502 A1 | * | 1/2002 | Nagaoka et al. | 428/198 |
| 2002/0026039 A1 | * | 2/2002 | Bellini et al. | 536/18.7 |
| 2002/0098764 A1 | * | 7/2002 | Mleziva et al. | 442/361 |
| 2002/0120291 A1 | * | 8/2002 | Shalaby | 606/230 |
| 2002/0168912 A1 | * | 11/2002 | Bond et al. | 442/415 |
| 2003/0035951 A1 | * | 2/2003 | Magill et al. | 428/373 |
| 2003/0039832 A1 | * | 2/2003 | Tsutsui et al. | 428/373 |
| 2003/0050666 A1 | * | 3/2003 | Grafton | 606/228 |
| 2003/0050667 A1 | * | 3/2003 | Grafton et al. | 606/228 |
| 2003/0092343 A1 | * | 5/2003 | Bond et al. | 442/361 |
| 2003/0139775 A1 | * | 7/2003 | Grafton | 606/228 |
| 2003/0148690 A1 | * | 8/2003 | Bond et al. | 442/338 |
| 2003/0203695 A1 | * | 10/2003 | Polanco et al. | 442/365 |
| 2003/0236553 A1 | * | 12/2003 | Knudsen | 606/228 |
| 2004/0126579 A1 | * | 7/2004 | Creagan | 428/373 |
| 2005/0031863 A1 | * | 2/2005 | Gownder et al. | 428/364 |
| 2005/0033362 A1 | * | 2/2005 | Grafton | 606/228 |
| 2005/0055051 A1 | * | 3/2005 | Grafton | 606/228 |
| 2005/0125036 A1 | * | 6/2005 | Roby | 606/228 |
| 2005/0149119 A1 | * | 7/2005 | Koyfman et al. | 606/228 |
| 2005/0164585 A1 | * | 7/2005 | Magill et al. | 442/361 |
| 2005/0208300 A1 | * | 9/2005 | Magill et al. | 428/364 |
| 2006/0052022 A1 | * | 3/2006 | Suzuki et al. | 442/328 |
| 2006/0084339 A1 | * | 4/2006 | Webb et al. | 442/329 |
| 2006/0089672 A1 | * | 4/2006 | Martinek | 606/228 |
| 2006/0142786 A1 | | 6/2006 | Mathisen et al. | |
| 2006/0155329 A1 | * | 7/2006 | Grafton et al. | 606/228 |
| 2006/0178701 A1 | * | 8/2006 | Schmieding | 606/228 |
| 2007/0135840 A1 | * | 6/2007 | Schmieding | 606/228 |
| 2007/0219568 A1 | * | 9/2007 | Yeo et al. | 606/151 |
| 2007/0260279 A1 | * | 11/2007 | Hotter et al. | 606/228 |
| 2007/0299542 A1 | | 12/2007 | Mathisen et al. | |
| 2008/0009903 A1 | * | 1/2008 | Schmieding et al. | 606/228 |
| 2008/0021501 A1 | * | 1/2008 | Schmieding | 606/228 |
| 2008/0051834 A1 | * | 2/2008 | Mazzocca et al. | 606/222 |
| 2008/0051835 A1 | * | 2/2008 | Mazzocca et al. | 606/222 |
| 2009/0035572 A1 | * | 2/2009 | Hotter et al. | 428/373 |
| 2009/0264925 A1 | * | 10/2009 | Hotter et al. | 606/228 |
| 2009/0275963 A1 | * | 11/2009 | May et al. | 606/151 |
| 2009/0275979 A1 | * | 11/2009 | Im et al. | 606/228 |
| 2010/0016891 A1 | * | 1/2010 | Kennedy et al. | 606/228 |
| 2010/0030261 A1 | * | 2/2010 | McClain | 606/230 |
| 2010/0274282 A1 | * | 10/2010 | Olson | 606/228 |
| 2011/0293936 A1 | * | 12/2011 | Bertsch et al. | 428/364 |
| 2012/0041483 A1 | * | 2/2012 | Indiano | 606/228 |
| 2012/0179198 A1 | * | 7/2012 | Schmieding et al. | 606/228 |
| 2012/0259360 A1 | * | 10/2012 | Mazzocca et al. | 606/229 |
| 2013/0211430 A1 | * | 8/2013 | Egnelov | 606/151 |
| 2013/0226234 A1 | * | 8/2013 | Avelar et al. | 606/231 |
| 2013/0315963 A1 | * | 11/2013 | Erneta et al. | 424/400 |

FOREIGN PATENT DOCUMENTS

| | | |
|---|---|---|
| WO | WO 03/092758 A1 | 11/2003 |
| WO | WO 2006/116000 A2 | 11/2006 |

* cited by examiner

MULTIFILAMENTS WITH TIME-DEPENDENT CHARACTERISTICS, AND MEDICAL PRODUCTS MADE FROM SUCH MULTIFILAMENTS

FIELD OF THE INVENTION

The present invention relates to a resorbable polymeric multifilament, and particularly to a resorbable polymeric multifilament with time-dependent characteristics, and even more particularly to a resorbable polymeric multifilament comprising at least two types of filaments having different degradation times and optionally also different moduli of elasticity. The invention is also directed to medical implants and products made from such resorbable polymeric multifilaments.

BACKGROUND OF THE INVENTION

Within the field of surgical repair of soft tissue defects such as hernias, use is often made of a mesh implant fabricated of a non-resorbable material that is inserted to cover the area of the tissue defect without sewing together the surrounding muscles. Such a mesh implant is most often made from various plastics, which are known to be biostable and safe for a number of years after implantation. However, it is known that such inert mesh materials can result in discomfort, inflammation, and recurrence of the hernia. Furthermore, permanently introducing a foreign material into the human (or animal) body could be accompanied with side effects such as migration, chronic inflammation, and chronic pain. The introduction of a relatively large inert implant is also likely to induce a long-term foreign-body-reaction caused by the body's immune defense system. As a result, the mesh implant may crumple up and lose its tissue supporting function.

An alternative approach is to make a mesh implant from a biodegradable polymer. Further, it is known to make a mesh implant from two different degradable polymers, either to improve the handling characteristics of such a mesh implant or to match the mechanical characteristics of such a mesh implant to the body's healing process of a hernia or other soft tissue defect.

For example, U.S. Pat. No. 6,162,962 to Hinsch et al. discloses an areal implant, which in one embodiment comprises a first resorbable polymer fiber arranged in a basic structure, into which a multifilament thread made from a second resorbable polymer has been woven for stiffening of the areal implant, to thereby facilitate handling during a medical implant procedure, e.g. when cutting to size and insertion. Here, the stiffening thread has a degradation time which is shorter than the degradation time of the polymer fibers of the basic structure.

Another example of degradable mesh implant is presented in U.S. Pat. No. 8,016,841, which is assigned to the present assignee and whose entire contents are incorporated herein by reference for the implant devices, techniques, materials, and methods disclosed therein. This patent describes a mesh implant made from at least two different polymeric fibers having different degradations times and also different moduli of elasticity, which are knitted together to form a mesh implant with time-dependent mechanical behavior. In this mesh implant, a first polymer fiber is arranged in a first knit pattern and a second polymer fiber is arranged in a second knit pattern, which is different from the first knit pattern and which locks movement of the first knit pattern. U.S. Published Applications 2006/0142786 and 2007/0299542 (now U.S. Pat. No. 8,083,755), which are assigned to the present assignee, also describe various implant devices, techniques, materials, and methods and their entire contents are incorporated herein by reference for the implant devices, techniques, materials, and methods disclosed therein.

SUMMARY OF THE INVENTION

Although the two patents listed above disclose two completely different ways of arranging two types of fibers in relation to each other; i.e. in U.S. Pat. No. 6,162,962 the two fibers are arranged in virtually the same pattern, whereas in U.S. Pat. No. 8,016,841 the two fibers are arranged in different patterns, the common feature is that the mechanical properties of the final products are determined by the specific knitting or weaving pattern(s) chosen for the particular manufacturing method. In other words, there are severe constraints regarding which knitting or weaving patterns can be utilized in practice. Consequently, there is a need for a more versatile and flexible solution.

Multifilaments as such are also more directly used in the medical healthcare industry; e.g. in the form of multifilament sutures, which are composed of several filaments twisted or braided together. Also resorbable polymeric multifilament sutures are known. These sutures are typically characterized by high initial tensile strength and are mainly absorbed by the human body by hydrolysis, during which process the suture loses tensile strength. The doctor or surgeon must however recognize that loss of tensile strength and the rate of absorption are separate phenomena, and the doctor or surgeon should further recognize that accelerated absorption may occur in patients with fever, infection, or protein deficiency, and may lead to an excessively rapid decline in tensile strength. To select the proper suture for a specific patient can therefore be a both delicate and difficult task, and consequently there is a need for a more robust and versatile suture or multifilament material.

The above objects are achieved by a resorbable polymeric multifilament as well as by a resorbable polymeric medical implant as described herein.

Embodiments of the present invention provide a multifilament which comprises at least two types of filaments having different degradation properties and optionally also different mechanical properties. The two types of filaments can be arranged in different geometrical cross-sectional patterns. The first filament type can, for example, occupy about one semicircle of a circular multifilament cross-section, while the second filament type occupies the complementary semicircle. In another arrangement, the two filament types can be arranged in a concentrical pattern, with filaments of the second type surrounding a core made up by filaments of the first type.

If a first filament type is characterized by a relatively short degradation time and a high modulus of elasticity, and a second filament type is characterized by a relatively long degradation time and low modulus of elasticity, it is according to embodiments of the present invention possible to compose a multifilament, which, when introduced into a human or animal body, initially has a high modulus of elasticity and at a later point in time, when the filaments of the first type have degraded, has a low modulus of elasticity. Multifilaments with such features can, for example, be used in medical multifilament polymer sutures used for soft tissue repair.

According to embodiments of the present invention a multifilament comprising at least two types of filaments can be knitted or woven to or into a medical device such as a medical mesh implant. If such a mesh implant is made from multifilaments comprising filaments of a first type, which is characterized by a relatively short degradation time and a high modulus of elasticity, and filaments of a second type, which is characterized by a relatively long degradation time and low modulus of elasticity, the mesh implant will, when implanted in a human or animal body, initially have a high modulus of elasticity and at a later point in time, when the filaments of the first type have degraded, have a low modulus of elasticity. Mesh implants with such features can, for example, be used for soft tissue repair. In contrast to existing mesh implants, e.g. mesh implants according to the teachings of the above-mentioned U.S. Pat. No. 8,016,841, mesh implants made from multifilaments according to the present invention can be manufactured by the use of virtually every known knitting or weaving technique which today is used for production of medical mesh implants.

DETAILED DESCRIPTION OF PREFERRED EMBODIMENTS

Figure 1:
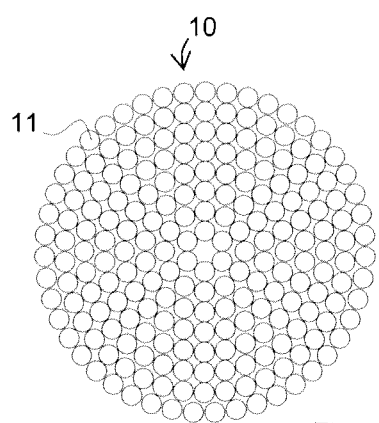
FIG. 1 illustrates a cross-section of a general multifilament, which belongs to the prior art and which is not part of the present invention.

FIG. 1 illustrates a cross-section of a general multifilament 10, which is not part of the present invention. The multifilament 10 comprises a number of individual filaments 11. The number of individual filaments 11 can principally assume any value, and may range from a few individual filaments to several hundred individual filaments. The filaments 11 can be made from natural or synthetic polymers or co-polymers or polymer compositions, and can be non-resorbable or resorbable, but in one single multifilament 10 all individual filaments 11 are made from the same polymer or copolymer or the same polymer composition.

Here, it may be mentioned that multifilaments made from a plurality of components are known. For example, U.S. patent application Ser. No. 11/054,195 to Schemken et al. discloses a method wherein a composite yarn is formed from a plurality of yarn components, which are spun, cooled, drawn, and textured in parallel relationship, and wherein at least one of the yarn components is drawn separately. This patent application is, however, silent about arranging filaments made from different kinds of polymers in the same multifilament.

Figure 2:
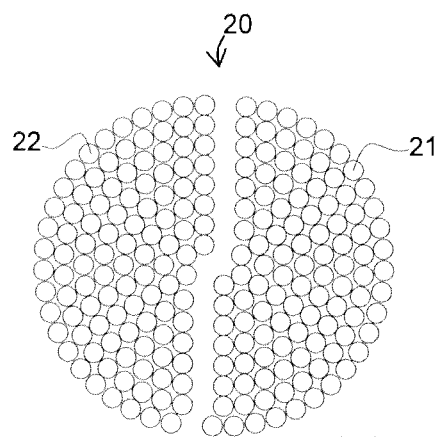
FIG. 2 shows a cross-section of a multifilament according to a first embodiment of the present invention, comprising two different types of filaments arranged in the shape of two semicircles.

In FIG. 2, a first embodiment of a multifilament 20 according to the present invention is schematically illustrated in cross-section. The multifilament 20 comprises a first type of individual filaments 21 and second type of individual filaments 22. In this particular embodiment, the multifilament 20 has a generally circular composite cross-section, whereof the individual filaments 21 of the first type contribute to about fifty percent (50%) of the total composite cross-sectional area and whereof the individual filaments 22 of the second type contribute to the remaining fifty percent (50%) of the total composite cross-sectional area. More specifically, the filaments 21 of the first type occupy about a full semi-circle (at the right-hand side in FIG. 2) of the total composite cross-section, and the filaments 22 of the second type occupy the complementary full semi-circle (at the left-hand side in FIG. 2) of the total composite cross-section.

Here it should be mentioned that FIG. 2 illustrates a multifilament having a rather ideal circular cross-sectional shape. In reality, a two-component multifilament arranged according to the basic principles shown in FIG. 2 can exhibit a less perfect cross-sectional shape, and can exhibit a more rectangular shape or square-like shape or a more irregular shape, the common feature being that filaments of a first type are arranged in a first geometrical cross-sectional arrangement and that filaments of a second type are arranged in a second geometrical cross-sectional arrangement, and that the two cross-sectional arrangements are arranged in close connection to each other. In accordance with the teachings of the first embodiment discussed in conjunction with FIG. 2, each of the two different filament types would however occupy about one continuous half of the total cross-section area. This type of a two-component multifilament according to the present invention can, for example, be manufactured by arranging a first spool or bobbin with a number of individual filaments of a first type and arranging a second spool or bobbin with a number of individual filaments of a second type, and in a parallel relationship bring together the two types of filaments into a single multifilament according to the first embodiment of the present invention. During the procedure, the resulting multifilament can be twisted to improve handling characteristics and also to ensure that the two types of filaments do not easily split up and separate from each other.

As stated above, in the embodiment shown in FIG. 2, the two different filament types each occupies about fifty percent (50%) of the total cross-section area. It is however within the scope of the present invention to let filaments of a first type occupy more than fifty percent (50%) of the total cross-section area; for example filaments of a first type can occupy any percentage (for example, any whole number) between 1% to 99% of the total cross-section area, while filaments of a second type occupy the remaining percentage of the total cross-section area. Also in cases where the two filament types occupy different percentages of the total cross-section area, the cross-sectional shape can be circular or rectangular, or can have any other regular or irregular shape. According to the present invention it is further possible that a multifilament has a total composite cross-section, in which individual filaments of a first type and/or a second type occupy a number of non-continuous portions of the composite cross-section. For example, filaments of a first type can form a continuous star-shaped cross-section with a number of star-arms, while cross-sections of filaments of a second type are disposed between the star-arms, thereby occupying non-continuous portions of the total composite cross-section.

Suitable polymers for the manufacture of filaments of the first type can preferably be resorbable polymers with a relatively short degradation time, and non-limiting examples are polymers or copolymers made from the monomer glycolide in pure form, or in combination with paradioxanone, lactide, trimethylene carbonate or caprolactone. Preferably glycolide is present in the highest concentration and can be combined with one or more of the other mentioned monomers in the same material. Yet another monomer can be paradioxanone in its pure form, or in combination with lactide, trimethylene carbonate or caprolactone. Suitable polymers for the manufacture of filaments of the second type can preferably be resorbable polymers with a relatively long degradation time, and non-limiting examples are polylactide and polyurethanes. Polylactide is preferably made from the monomer L,L-lactide, which can be combined with small amounts of other monomers such as glycolide, trimethylene carbonate or caprolactone to fine tune elastic and degradation properties. Examples of degradable polyurethanes are, but not limited to, polyureaurethanes, polyesterurethanes and polycarbonateurethanes. If it is desired to provide a two-component multifilament, which initially, when implanted in a human body, has a high modulus of elasticity and which at a later point in time, when the filaments of the first type have degraded, has a low modulus of elasticity, the polymers of the first type of filaments should be characterized by a high modulus of elasticity while the polymers of the second type of filaments should be characterized by a low modulus of elasticity. Suitable polymer combinations would, for example, be polyglycolide or blockcopolymers where the main monomer component being glycolide in combination with a small amount of trimethylene carbonate or caprolactone for the first polymer type and blockcopolymers with L,L-lactide as the main monomer component in combination with trimethylene carbonate or caprolactone. Various polyesterurethanes and polycarbonateurethanes would also be of particular use in certain applications, with their long in vivo degradation time and high elasticity, for the second polymer type.

Figure 3:
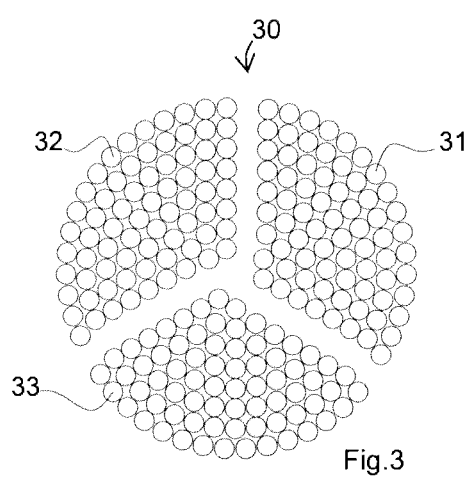
FIG. 3 shows a cross-section of a multifilament according to a second embodiment of the present invention, comprising three different types of filaments arranged in the shape of three circle sectors.

In FIG. 3, a second embodiment of a multifilament 30 according to the present invention is schematically illustrated in cross-section. The multifilament 30 comprises a first type of individual filaments 31, a second type of individual filaments 32, and a third type of individual filaments 33. In this particular embodiment, the multifilament 30 has a generally circular total composite cross-section, wherein the individual filaments 31 of the first type contribute to about a first third (33%) of the total cross-sectional area, and wherein the individual filaments 32 of the second type contribute to about a second third (33%) of the total cross-sectional area, and wherein the individual filaments 33 of the third type contribute to the remaining third (33%) of the total cross-sectional area. More specifically, the filaments 31 of the first type assume the shape of a circle sector (upper right-hand side in FIG. 3) that occupies about a third of the total circular cross-section area, while the filaments 32 of the second type assume the shape of a circle sector (upper left-hand side in FIG. 3) that also occupies about a third of the total circular cross-section area, and while the filaments 33 of the third type also assume the shape of a circle sector (lower part in FIG. 3) that occupies the remaining and last third of the total circular cross-section area.

Here it should be mentioned that FIG. 3 illustrates a rather ideal circular composite cross-sectional shape. In reality, a three-component multifilament arranged according to the basic principles shown in FIG. 3 can exhibit a less perfect cross-sectional shape, and can exhibit a more rectangular shape or square-like shape or a more irregular shape. In accordance with the teachings of the second embodiment discussed in conjunction with FIG. 3, each of the three different filament types would however occupy about one continuous third of the total cross-section area. This type of a three-component multifilament according to the present invention can, for example, be manufactured by arranging a first spool or bobbin with a number of individual filaments of a first type and arranging a second spool or bobbin with a number of individual filaments of a second type and arranging a third spool or bobbin with a number of individual filaments of a third type, and in a parallel relationship bring together the three types of filaments into a single multifilament according to the principles discussed in conjunction with the first embodiment of the present invention. During the procedure, the resulting multifilament can be twisted to improve handling characteristics and also to ensure that the three types of multifilaments do not easily split up and separate from each other.

As stated above, in the embodiment shown in FIG. 3, the three different filament types each occupies about a third (33%) of the total cross-section area. It is however within the scope of the present invention to let filaments of a first type occupy more or less than a third of the total composite cross-section area, and also filaments of the second and third types can occupy more or less than a third of the total composite cross-section area. Filaments of any specific type can, for example, occupy any percentage (for example any whole number) between 2% to 98% of the total composite cross-section area. Also in cases where the three filament types occupy different percentages of the total cross-section area, the cross-sectional shape can be circular or rectangular, or can have any other regular or irregular shape. According to the present invention it is further possible that a multifilament has a total composite cross-section, in which individual filaments of a first type and/or a second type and/or a third type occupy a number of non-continuous portions of the composite cross-section.

Suitable polymers for the manufacture of filaments of the first type can preferably be resorbable polymers with a relatively short degradation time, and non-limiting examples are polymers or copolymers made from the monomer glycolide in pure form or in combination with paradioxanone, lactide, trimethylene carbonate or caprolactone. Preferably glycolide is present in the highest concentration and can be combined with one or more of the other mentioned monomers in the same material. Suitable polymers for the manufacture of filaments of the second type can preferably be resorbable polymers with a relatively longer degradation time, and non-limiting examples are polyparadioxanone and blockcopolymers of glycolide having a relative high content of trimethylene carbonate in the center segment. Also various copolymers of lactide in combination with trimethylene carbonate and/or caprolactone to increase elasticity and reduce degradation times are preferable. Suitable polymers for the manufacture of filaments of the third type can preferably be resorbable polymers with the relatively longest degradation time, and non-limiting examples are polylactide and polyurethanes. Polylactide is preferably made from the monomer L,L-lactide which can be combined with small amounts of other monomers such as glycolide, trimethylene carbonate or caprolactone to fine tune elastic and degradation properties. Examples of degradable polyurethanes are, but not limited to, polyureaurethanes, polyesterurethanes and polycarbonateurethanes. If it is desired to provide a three-component multifilament which initially when implanted in a human body has a high modulus of elasticity and which at a later point in time, when the filaments of the first type have degraded, has a lower modulus of elasticity, and at an even later point in time, when also the filaments of the second type have degraded, has an even lower modulus of elasticity, the polymers of the first type of filaments should be characterized by a high modulus of elasticity, while the polymers of the second type of filaments should be characterized by a relatively lower modulus of elasticity, and while the polymers of the third type of filaments should be characterized by the relatively lowest modulus of elasticity. Suitable polymer combinations would, for example, be polymers or copolymers made from the monomer glycolide in pure form or in combination with paradioxanone, lactide, trimethylene carbonate or caprolactone. Preferably glycolide is present in the highest concentration and can be combined with one or more of the other mentioned monomers in the same material. Suitable polymers for the first polymer type are polyparadioxanone and blockcopolymers of glycolide having a relative high content of trimethylene carbonate in the center segment. Also various copolymers of lactide in combination with trimethylene carbonate and/or caprolactone to increase elasticity and reduce degradation times are preferable. Suitable polymers for the second polymer type are polylactide and polyurethanes. Polylactide is preferably made from the monomer L,L-lactide which can be combined with small amounts of other monomers such as glycolide, trimethylene carbonate or caprolactone to fine tune elastic and degradation properties. Examples of degradable polyurethanes are, but not limited to, polyureaurethanes, polyesterurethanes and polycarbonateurethanes for the third polymer type.

Figure 4:
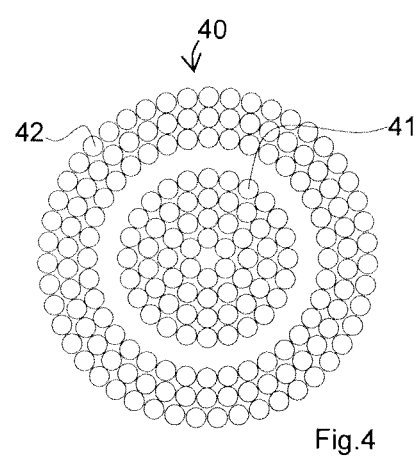
FIG. 4 shows a cross-section of a multifilament according to a third embodiment of the present invention, comprising two different types of filaments disposed in a concentrical arrangement.

In FIG. 4, a third embodiment of a multifilament 40 according to the present invention is schematically illustrated in cross-section. The multifilament 40 comprises a first type of individual filaments 41 and second type of individual filaments 42. In this particular embodiment, the multifilament 40 has a generally circular composite cross-section, wherein the individual filaments 41 of the first type constitute the core of the composite cross-section and wherein the individual filaments 42 of the second type are arranged in a concentrical arrangement with the individual filaments 42 of the second type disposed in a circular shell around the core of individual filaments 41 of the first type. For illustrative purposes only, in FIG. 4 there is an empty gap between the core and the circular shell; in reality this gap can be infinitely small, e.g. non-existing.

Here it should be mentioned that FIG. 4 illustrates a multifilament having a rather ideal circular cross-sectional shape. In reality, a two-component multifilament arranged according to the basic principles shown in FIG. 4 can exhibit a less perfect shape, and can exhibit a more irregular shape, the common feature still being that individual filaments of a second type are arranged around and at least partly cover individual filaments of a first type. This type of a two-component multifilament according to the third embodiment of the present invention can, for example, be manufactured by arranging a first spool or bobbin with a number of individual filaments of a first type and arranging a second spool or bobbin with a number of individual filaments of a second type, and by, for example, providing a nozzle or other device by which the filaments of the second type are guided and distributed over a core made up of the filaments of the first type. By this production method, the individual filaments of both the first and second types can be manufactured by, for example, melt extrusion at an earlier point in time.

Suitable exemplifying polymers and polymer combinations for the manufacture of a multifilament according to this third embodiment are the same as discussed above in conjunction with the first embodiment of the invention shown in FIG. 2. However, care should be taken (in light of the specific medical use of the multifilament) when choosing the specific polymer and filament configuration, i.e. if a first resorbable polymer having a relatively short degradation time is chosen for the multifilament core and second resorbable polymer having a relatively long degradation time is chosen for the filament circumference, a hollow multifilament will be the temporary result when the core has degraded; whereas a thinner multifilament will be the temporary result if a polymer with relatively short degradation time is chosen for the filament circumference provided around a filament core made from a polymer with a relatively long degradation time.

Figure 5:
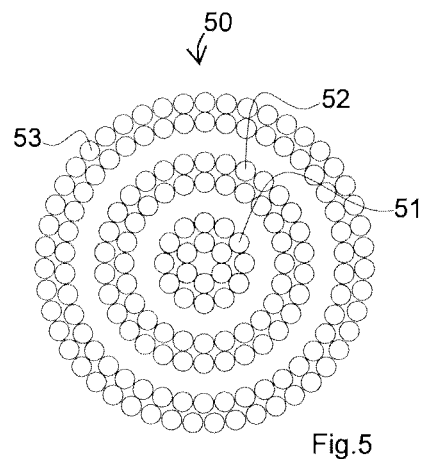
FIG. 5 shows a cross-section of a multifilament according to a fourth embodiment of the present invention, comprising three different types of filaments disposed in a concentrical arrangement.

In FIG. 5, a fourth embodiment of a multifilament 50 according to the present invention is schematically illustrated in cross-section. The multifilament 50 comprises individual filaments 51 of a first type, individual filaments 52 of a second type, and individual filaments 53 of a third type. In this particular embodiment, the multifilament 50 has a generally circular composite cross-section, wherein the individual filaments 51 of the first type constitute the core of the composite cross-section and wherein the individual filaments 52 of the second type are arranged in a concentrical arrangement with the individual filaments 52 of the second type disposed around the core of individual filaments 51 of the first type, and wherein the filaments 53 of the third type are arranged in a concentrical arrangement with individual filaments 53 of the third type disposed around the individual filaments 52 of the second type. Thus, the individual filaments 52 constitute an inner circular shell and the individual filaments 53 constitute an outer circular shell, both shells being concentrically arranged around a common core of individual filaments 51. For illustrative purposes only, in FIG. 4 there are empty gaps between the core and the inner circular shell as well as between the inner circular shell and the outer circular shell. In reality these gaps can be infinitely small, e.g. non-existing.

Suitable exemplifying polymers and polymer combinations for the manufacture of a multifilament according to this fourth embodiment are the same as discussed above in conjunction with the second embodiment of the invention shown in FIG. 3. However, the same considerations apply here regarding the choice of specific polymer configurations as was discussed in conjunction with the third embodiment shown in FIG. 4, i.e. if a resorbable polymer having the relatively shortest degradation time is provided as polymer filaments arranged in a core, a hollow multifilament will be the temporary result when the core has degraded; and if instead a resorbable polymer having the relatively shortest degradation time is provided as polymer filaments arranged as an inner circular shell, a hollow multifilament, with a core and an outer circular shell and a gap therebetween, will be the temporary result when the inner circular shell has degraded.

A common and very important feature for all embodiments of the present invention is that the relative cross-sectional positions for the individual filaments of any type remain the same wherever a cross-section is taken along the length of a multifilament according to the present invention. This invariant cross-section feature prevails even if, for example, a multifilament is twisted during the production thereof.

It will be understood that the invention is not restricted to the above described exemplifying embodiments thereof and that many modifications are possible. In particular, it should be understood that more than three different polymer filaments can be arranged in a basically parallel relationship, as exemplified by the first and second embodiments shown in FIG. 2 and FIG. 3, respectively, or in a basically concentric relationship, as exemplified by the third and fourth embodiments shown in FIG. 4 and FIG. 5, respectively. It should also be mentioned that herein the terms "resorbable", "absorbable", "degradable" and "biodegradable" are used interchangeably, and all refer to filaments or multifilaments and medical products made thereof which degrade in a human or animal body.

Multifilaments according to the present invention can be used directly in medical sutures, i.e. a single multifilament can be used as a suture, or several multifilaments can be twisted or braided together to form a suture. When implanted in a human or animal body, such a suture will degrade with time, and will in particular exhibit time-dependent characteristics; for example become more elastic when filaments of a first type having a short degradation time and high modulus of elasticity have degraded and only filaments of a second type, having longer degradation time and a low modulus of elasticity, remain in the human or animal body. Such a multifilament can thereby be adapted to the body's healing process, i.e. initially be relatively inelastic when the damaged tissue needs full support and gradually lose strength as the tissue heals and becomes stronger. An important feature of multifilaments according to the present invention is that an outer surface of the multifilament can be made very smooth and regular. Due to this smooth and regular outer surface, a multifilament according to the present invention can be used in virtually all types of knitting or weaving machines that today are used to, for example, produce medical implant devices. This is in contrast to braided, twisted multifilaments according to prior art, which would get stuck in most known knitting or weaving machines.

Resorbable multifilaments according to the present invention can also be used in medical products such as medical mesh implants, wherein several multifilaments are woven or knitted together to form a resorbable mesh implant. Such a medical mesh implant will then exhibit time-dependent characteristics, e.g. become more elastic when filaments of a first type, having short degradation time and a high modulus of elasticity, have degraded and only filaments of a second type, having longer degradation time and a low modulus of elasticity, remain in the human or animal body. Such a resorbable mesh can thereby be adapted to the body's healing process, i.e. initially be relatively inelastic when the damaged tissue needs full support and gradually lose strength as the tissue heals and becomes stronger. Such time-dependent characteristics can be achieved with virtually any known knitting or weaving technique, i.e. the time-dependent characteristics are not dependent on a particular knitting or weaving pattern. This last feature is in contrast to known medical mesh implants, wherein specific time-dependent mechanical characteristics can only be achieved by selecting specific knitting or weaving patterns, which may include a first specific knitting or weaving pattern for a first type of fibers, filaments or multifilaments having a relatively short degradation time and another specific knitting or weaving pattern for a second type of fibers, filaments or multifilaments having a relatively longer degradation time.

What is claimed is:

1. An implantable, synthetic, resorbable multifilament, comprising:
   a number of individual resorbable filaments of a first type having a first degradation time, and
   a number of individual resorbable filaments of a second type having a second degradation time; wherein
   the second degradation time is different from the first degradation time; and wherein
   the filaments of the first type and the filaments of the second type are arranged in close relationship to form an implantable, synthetic, composite multifilament having a length and a specific composite cross-section, which comprises cross-sections of the individual filaments of the first type and cross-sections of the individual filaments of the second type; wherein
   the cross-sections of the individual filaments of the first and second types are located at determined relative positions; and wherein
   the relative positions amongst the individual cross-sections of the filaments of the first type and the individual cross-sections of the filaments of the second type are invariant over the length of the composite multifilament.

2. The implantable, synthetic, resorbable multifilament according to claim 1, wherein the individual filaments of the first type have a first modulus of elasticity and the individual filaments of the second type have a second modulus of elasticity, and wherein the second modulus of elasticity is different from the first modulus of elasticity.

3. The implantable, synthetic, resorbable multifilament according to claim 1, wherein the filaments of the first type occupy a first continuous portion of the composite cross-section.

4. The implantable, synthetic, resorbable multifilament according to claim 1, wherein the filaments of the first type occupy a number of non-continuous portions of the composite cross-section.

5. The implantable, synthetic, resorbable multifilament according to claim 1, wherein the multifilament has a generally circular cross-section, and wherein the filaments of the first type occupy a first circle sector of the circular cross-section and the filaments of the second type occupy a second circle sector of the circular cross-section.

6. The implantable, synthetic, resorbable multifilament according to claim 5, wherein the first circle sector is a semicircle and the second circle sector is a complementary semicircle.

7. The implantable, synthetic, resorbable multifilament according to claim 1, wherein the multifilament has a generally circular cross-section, and wherein the filaments of the first type constitute a core of the circular cross-section and the filaments of the second type are disposed concentrically around the core.

8. The implantable, synthetic, resorbable multifilament according to claim 1, wherein the multifilament has a generally circular cross-section, and wherein the filaments of the first type constitute a core of the composite cross-section and the filaments of the second type are disposed concentrically around the core, and wherein the first degradation time is longer than the second degradation time.

9. The implantable, synthetic, resorbable multifilament according to claim 8, wherein the individual filaments of the first type have a first modulus of elasticity and the individual filaments of the second type have a second modulus of elasticity, and wherein the first modulus of elasticity is lower than the second modulus of elasticity.

10. The implantable, synthetic, resorbable multifilament according to claim 1, wherein the multifilament has a generally circular cross-section, and wherein the filaments of the first type constitute a core of the composite cross-section and the filaments of the second type are disposed concentrically around the core, and wherein the first degradation time is shorter than the second degradation time.

11. The implantable, synthetic, resorbable multifilament according to claim 10, wherein the individual filaments of the first type have a first modulus of elasticity and the individual filaments of the second type have a second modulus of elasticity, and wherein the first modulus of elasticity is higher than the second modulus of elasticity.

12. An implantable, synthetic, resorbable multifilament, comprising:
   a number of individual resorbable filaments of a first type having a first degradation time, and
   a number of individual resorbable filaments of a second type having a second degradation time, and
   a number of individual resorbable filaments of a third type having a third degradation time; wherein the second degradation time is different from the first degradation time, and the third degradation time is different from the second degradation time and is also different from the first degradation time; and wherein the filaments of the first type, the filaments of the second type and the filaments of the third type are arranged in close relationship to form an implantable, synthetic, composite multifilament having a length and a specific cross-section, which comprises cross-sections of the individual filaments of the first type, cross-sections of the individual filaments of the second type and cross-sections of the individual filaments of the third type; wherein the cross-sections of the individual filaments of the first, second and third types are located at determined relative positions; and wherein the relative positions amongst the individual cross-sections of the filaments of the first type, the individual cross-sections of the filaments of the second type and the individual cross-sections of the filaments of the third type are invariant over the length of the composite multifilament.

13. The implantable, synthetic, resorbable multifilament according to claim 12, wherein the individual filaments of the first type have a first modulus of elasticity, the individual filaments of the second type have a second modulus of elasticity and the individual filaments of the third type have a third modulus of elasticity, and wherein the second modulus of elasticity is different from the first modulus of elasticity and the third modulus of elasticity is different from the second modulus of elasticity and is also different from the first modulus of elasticity.

14. The implantable, synthetic, resorbable multifilament according to claim 12, wherein the multifilament has a generally circular cross-section, and wherein the filaments of the first type occupy a first circle sector of the circular cross-section, the filaments of the second type occupy a second circle sector of the circular cross-section and the filaments of the third type occupy a third circle sector of the circular cross-section.

15. The implantable, synthetic, resorbable multifilament according to claim 12, wherein the multifilament has a generally circular cross-section, and wherein the filaments of the first type constitute a core of the composite cross-section, the filaments of the second type are disposed concentrically around the core and the filaments of the third type are disposed concentrically around the filaments of the second type.

16. The implantable, synthetic, resorbable multifilament according to claim 15, wherein the third degradation time is shorter than the second degradation time and the second degradation time is shorter than the first degradation time.

17. The implantable, synthetic, resorbable multifilament according to claim 16, wherein the individual filaments of the first type have a first modulus of elasticity, the individual filaments of the second type have a second modulus of elasticity and the individual filaments of the third type have a third modulus of elasticity, and wherein the first modulus of elasticity is lower than the second modulus of elasticity and the second modulus of elasticity is lower than the third modulus of elasticity.

18. A medical mesh comprising implantable, synthetic, resorbable multifilaments according to claim 1 configured in a woven mesh configured for implantation in a human body.

19. A medical mesh comprising the implantable, synthetic, resorbable multifilament according to claim 12.

* * * * *